United States Patent [19]
Yokozeki et al.

[11] Patent Number: 4,968,606
[45] Date of Patent: Nov. 6, 1990

[54] METHODS FOR PRODUCING RIBOSE-1-PHOSPHORIC ACID AND RIBAVIRIN

[75] Inventors: Kenzo Yokozeki; Hideyuki Shirae; Koji Kubota, all of Kawasaki, Japan

[73] Assignee: Ajinomoto Co., Inc., Tokyo, Japan

[21] Appl. No.: 407,697

[22] Filed: Sep. 15, 1989

Related U.S. Application Data

[63] Continuation of Ser. No. 141,428, Jan. 7, 1988, abandoned.

[30] Foreign Application Priority Data

Jan. 19, 1987 [JP] Japan ................. 62-009652

[51] Int. Cl.$^5$ .............. C12P 19/38; C12P 39/00; C12R 1/07; C12R 1/22
[52] U.S. Cl. ........................... 435/42; 435/85; 435/87; 435/847; 435/852
[58] Field of Search .............. 435/42, 85, 87, 847, 435/852

[56] References Cited

U.S. PATENT DOCUMENTS 4,458,016  7/1984  Yamanaka et al. ............ 435/85
4,614,719  9/1986  Fujishima et al. ............ 435/85

OTHER PUBLICATIONS

Derwent Abs 84-240648/39, Yamasa Shoyu, J59143599 (8-1984).
Biotech 85-133880, Yoshihisa et al., J60133880 (7-1985).
Derwent Abs 84-291215/49, Yamasa Shoyu, J59179094 (10-1984).
Biotech 84-006895, Fujishima, J59006895 (1-1984).
Derwent Abs 78-04939A/03, Kyowa Hakkokogyo, J50135287 (10-75).
Biotech 83-216696, Fujishima et al., (J58216696)(12-1983).
Biotech 88-05074, Shirae et al., Agric. Biol. Chem. (1988) 52,1,295-296.
Biotech 85-133896, Fujishima et al., ·J60133896 (7-1985).
K. F. Jensen, *Biochimica et Biophysica Acta*, vol. 525, pp. 346-356 (1978).
*ATCC Catalogue of Bacteria Phages rDNA Vectors*, R. Gherna et al., Eds. p. 87 (1985).
T. P. Zimmerman et al., *Canadian Journal of Biochemistry*, vol. 49, pp. 1050-1054 (1971).
Senesi et al., *FEBS Letters*, vol. 64, No. 2, pp. 353-357, May 1976.
R. L. Miller et al., *Biochemical Pharmacology*, vol. 36, No. 4, pp. 553-560, (1987).

*Primary Examiner*—Herbert J. Lilling
*Attorney, Agent, or Firm*—Oblon, Spivak, McClelland, Maier & Neustadt

[57] ABSTRACT

The present invention relates to methods for producing ribavirin utilizing microorganisms and a method for producing ribose-1-phosphoric acid which is a precursor of ribavirin. The methods involve contacting certain microorganisms with orotidine, orotidic acid, or salts thereof, and inorganic phosphoric acid or a salt thereof (to produce ribose-1-phosphoric acid), and further with 1,2,4-triazole-3-carboxamide or a salt thereof (to produce ribavirin) in an aqueous solvent.

4 Claims, No Drawings

METHODS FOR PRODUCING RIBOSE-1-PHOSPHORIC ACID AND RIBAVIRIN

This application is a continuation of application Ser. No. 07/141,428, filed on Jan. 7, 1988, now abandoned.

BACKGROUND OF THE INVENTION

1. Field of the Invention

Ribavirin (1-$\beta$-D-ribofuranosyl-1,2,4-triazole-3-carboxamide) possesses an antiviral activity and can be utilized as a drug.

The present invention relates to methods for producing ribavirin utilizing microorganisms and a method for producing ribose-1-phosphoric acid which is a precursor of ribavirin.

2. Description of the Related Art

It is known that ribavirin can be prepared not only by chemical synthesis but also by biochemical reactions (Published Examined Japanese patent application No. 17830/79, Published Unexamined Japanese patent application Nos. 146593/82, 190396/83, 216696/83, 6895/84, 143599/84, 120981/85, 133896/85, etc.). These methods include a fermentation method which comprises culturing a microorganism in a medium containing a triazole derivative to produce ribavirin and an enzymatic method which comprises allowing a microorganism cell to act on a 1,2,4-triazole derivative and a ribose donor to produce ribavirin.

In any of these methods, the yield of ribavirin is unsatisfactory and it has been desired to develop a method for efficiently producing ribavirin in a high yield.

SUMMARY OF THE INVENTION

As a result of extensive investigations to achieve such an object, the present inventors have found that the production yield of ribavirin can be markedly improved by using orotidine or orotidic acid as a substrate and based on this finding, have accomplished the present invention.

To produce ribavirin according to the methods of the present invention, first there is a method for producing ribose-1-phosphoric acid as a precursor of ribavirin which comprises contacting orotidine or orotidic acid and inorganic phosphoric acid with microorganisms.

The microorganisms used for this method are those belonging to the genus Arthrobacter, the genus Bacillus, the genus Cellulomonas, the genus Brevibacterium, the genus Corynebacterium, the genus Escherichia, the genus Nocardia, the genus Planococcus, the genus Pseudomonas, the genus Vibrio, the genus Xanthomonas, the genus Serratia, the genus Streptomyces, and the genus Erwinia which are capable of producing ribose-1-phosphoric acid from orotidine or orotidic acid or salts thereof and inorganic phosphoric acid or salts thereof. Examples of such microorganisms include:

| | |
|---|---|
| Arthrobacter citreus | ATCC 11624 |
| Bacillus subtilis | IFO 3134 |
| Cellulomonas flavigena | ATCC 488 |
| Brevibacterium ammoniagenes | ATCC 6872 |
| Corynebacterium flavescens | ATCC 10340 |
| Escherichia coli | ATCC 12814 |
| Nocardia asteroides | ATCC 19247 |
| Planococcus eucinatus | FERM P-9133 |
| Pseudomonas rubescens | ATCC 12099 |
| Vibrio metschnikovii | ATCC 7708 |
| Xanthomonas campestris | ATCC 11765 |
| Serratia rubefaciens | FERM P-9134 |
| Streptomyces tanashiensis | ATCC 15238 |
| Erwinia carotovora | FERM P-9135, FERM BP-1538 |

The strain identified above by FERM P-9135 was originally deposited on Jan. 19, 1987 at the Fermentation Research Institute, Agency of Industrial and Technology, Ministry Of International Trade and Industry (FRI), 1-3, Higashi 1-chome, Tsukuba-shi, Ibaragi-ken 305, Japan, and was accorded the accession number FERM P9135 indicated above. The strain deposit was then converted into a deposit under the Budapest Treaty on Oct. 27, 1987, and was accorded the corresponding accession number FERM BP-1538.

To obtain bacterial cells of these microorganisms, these microorganisms may be cultured in ordinary media containing carbon sources, nitrogen sources, inorganic ions and if necessary and desired, organic trace nutrients such as vitamins, etc. No particular method is required for the culture but conventionally known methods can be appropriately adopted.

As cells, the culture solution obtained by the methods described above can be used as it is; alternatively, washed cells can be used and cell treated matters can also be used. As the cell treated matters, there can be used cells dried with acetone, homogenized cells, cells treated with ultrasonic waves, cells obtained by contacting them with surface active agents, toluene, or the like; cells treated with enzymes such as lysozyme, or the like; protein fraction(s) of cells obtained by extraction from the cells and isolation by salting-out, etc.; purified protein fraction(s) having an enzymatic activity of the present reaction; and the aforesaid cells or cell treated matters immobilized with natural or synthetic polymers, etc.

Orotidic acid used for these methods may be unmodified or modified, e.g., by phosphorylation of one, two or all of the hydroxy group(s) of orotidine at the 2-, 3- or 5-position thereof to form the monophosphate, diphosphate or triphosphate.

The salts of orotidine or orotidic acid may be any salts as far as they do not markedly inhibit the progress of the reaction. For example, the salts may be salts of inorganic bases such as sodium salts, calcium salts, magnesium salts, etc.; salts of organic bases such as triethylammonium salts, etc.

It is appropriate that the concentration of orotidine or orotidic acid or salts thereof be approximately 1 to 1000 mM. It is preferred that the concentration of the inorganic phosphoric acid or salts thereof be in an amount equimolar to or larger than orotidine or orotidic acid or salts thereof, suitably about 1 to about 10 times. Orotidine and orotidic acid can be used in combination and in this case, the concentration described above is the sum of both. The cells of microorganisms described above or treated matters thereof are added to an aqueous solution containing orotidine or orotidic acid or salts thereof. After adjusting pH to a range of 4 to 10, the mixture is maintained at 20° to 70° C., desirably 50° to 70° C., for 10 minutes to 5 days, with appropriate agitation, whereby the reaction proceeds and marked amounts of the desired ribose-1-phosphoric acid can be accumulated in the reaction solution.

To collect ribose-1-phosphoric acid from the reaction solution, a method of utilizing a difference in solubility in solvents such as water, etc. or a method of using ion exchange resins, etc. can be adopted.

The produced ribose-1-phosphoric acid is reacted with the 1,2,4-triazole derivative, after or without isolation from the reaction solution, to produce ribavirin.

The microorganisms utilized at this stage are those belonging to the genus Pseudomonas, the genus Flavobacterium, the genus Achromobacter, the genus Salmonella, the genus Citrobacter, the genus Escherichia, the genus Sporosarcina, the genus Alcaligenes, the genus Enterobacter, the genus Aeromonas, the genus Arthrobacter, the genus Brevibacterium, the genus Serratia, the genus Erwinia, the genus Proteus, the genus Corynebacterium, the genus Cellulomonas, the genus Xanthomonas, the genus Klebsiella, the genus Micrococcus, the genus Bacillus, the genus Bacterium, the genus Candida, the genus Saccharomyces, the genus Staphylococcus, the genus Kurthia, the genus Vibrio or the genus Mycoplana, which are capable of producing ribavirin from ribose-1-phosphoric acid or salts thereof and 1,2,4-triazole-3-carboxamide or salts thereof. Examples of such microorganisms include:

| | |
|---|---|
| Pseudomonas diminuta | ATCC 11568 |
| Flavobacterium rhenanum | CCM 298 |
| Achromobacter lacticum | CCM 69 |
| Salmonella schottmuelleri | ATCC 8759 |
| Erwinia herbicola | ATCC 14536 |
| Proteus vulgaris | FERM P-4795 |
| Bacterium cadaveria | ATCC 9760 |
| Xanthomonas citri | FERM P-3396 |
| Citrobacter freundii | ATCC 8090 |
| Mycoplana dimorpha | ATCC 4279 |
| Escherichia coli | ATCC 10798 |
| Enterobacter cloacae | ATCC 13047 |
| Serratia marcescens | IFO 3046 |
| Klebsiella pneumoniae | ATCC 9621 |
| Micrococcus luteus | ATCC 398 |
| Cornyebacterium michiganense | ATCC 7429 |
| Bacillus brevis | ATCC 8185 |
| Cellulomonas flavigena | ATCC 8183 |
| Arthrobacter globiformis | ATCC 8010 |
| Brevibacterium ammoniagenes | ATCC 6871 |
| Alcaligenes metalcaligenes | ATCC 13270 |
| Sporosarcina ureae | ATCC 6473 |
| Aeromonas salmonicida | ATCC 14174 |
| Candida tropicalis | ATCC 14056 |
| Saccharomyces cerevisiae | ATCC 2601 |
| Staphylococcus epidermidis | ATCC 155 |
| Kurthia zophii | ATCC 6900 |
| Vibrio metchnikovii | ATCC 7708 |

The mode of collection and use of these microorganism cells may be the same as described above; for example, the mode of use includes cell treated matters and solids thereof.

The salts of ribose-1-phosphoric acid and 1,2,4-triazole-3-carboxamide may be any salts as far as they do not markedly inhibit the progress of the reaction; for example inorganic bases or organic bases described with respect to orotidic acid, etc. can also be used.

It is appropriate that the concentration of ribose-1-phosphoric acid or salts thereof be approximately 1 to 1000 mM. It is preferred that the concentration of 1,2,4-triazole-3-carboxamide or salts thereof be in an amount of approximately 0.5 to 2 times the number of moles of ribose-1-phosphoric acid or salts thereof, generally suitably almost equimolar thereto. Reaction procedures, reaction conditions and collection of ribavirin from the reaction solution may be similar to the reaction of producing ribose1-phosphoric acid described above.

It is preferred that the reaction of producing ribose-1-phosphoric acid at the former stage proceed continuously with the reaction of producing ribavirin at the latter stage. In this case, it is convenient to carry out both reactions at once by contacting the microorganisms at the step described above on orotidine or orotidic acid or salts thereof and the inorganic phosphoric acid or salts thereof as well as 1,2,4-triazole-3 carboxamide or salts thereof, in one reactor.

On the other hand, microorganisms capable of carrying out the two reactions described above simultaneously (having enzymes that catalyze both reactions) can also be used and acted on an aqueous solution containing orotidine or orotidic acid or salts thereof and the inorganic phosphoric acids or salts thereof as well as 1,2,4-triazole-3-carboxamide or salts thereof thereby to produce ribavirin in one mixture.

The microorganisms used for this method are those belonging to the genus Bacillus, the genus Escherichia, the genus Planococcus, the genus Pseudomonas, the genus Vibrio, the genus Serratia or the genus Erwinia, which are capable of producing ribavirin from orotidine or orotidic acid or salts thereof and an inorganic phosphoric acid or salts thereof as well as 1,2,4-triazole-3-carboxamide or salts thereof. Examples of such microorganisms include:

| | |
|---|---|
| Bacillus subtilis | IFO 3134 |
| Escherichia coli | ATCC 12814 |
| Planococcus eucinatus | FERM P-9133 |
| Pseudomonas rubescens | ATCC 12099 |
| Vibrio metschnikovii | ATCC 7708 |
| Serratia rubefaciens | FERM P-9134 |
| Erwinia carotovora | FERM P-9135, FERM BP-1538 |

The mode of collection and use of these microorganism cells, the content of substrate aqueous solutions, the reaction procedures and mode of collection of ribavirin from the reaction solution may be carried out in a manner similar to those described above.

When the microorganisms capable of producing ribose-1-phosphoric acid are caused to act on orotidine or orotodic acid and inorganic phosphoric acids, orotidine, orotidic acid or orotidic acid residues are released, whereby the phosphoric acid residue is replaced therefor. In this case, orotidic acid releases the phosphoric acid residue at the 2-, 3- or 5-position thereof.

When the microorganisms capable of producing ribavirin from ribose-1-phosphoric acid and 1,2,4-triazole-3-carboxamide are used, the phosphoric acid residue of ribose-1-phosphoric acid is split off and 1,2,4-triazole-3-carboxamide is introduced in its place.

It is assumed that the microorganisms capable of producing ribavirin from orotidine or orotidic acid and inorganic phosphoric acid as well as 1,2,4-triazole-3carboxamide have both enzymes and therefore carry out the reaction continuously.

The invention now being generally described, the same will be better understood by reference to certain specific examples which are included herein for purposes of illustration only and are not intended to be limiting of the invention or any embodiment thereof, unless specified.

EXAMPLES

Example 1

In a 500 ml flask with a shoulder was charged 50 ml of a medium (pH 7.0) containing 0.5 g/dl of yeast extract, 1.0 g/dl of peptone, 1.0 g/dl of meat extract and 0.5 g/dl of NaCl followed by sterilization. One platinum earpick each of microorganisms shown in Table 1 was inoculated and shake cultured at 30° C. for 16 hours.

After centrifugation of 5 ml of the obtained culture solution, washing was performed with 0.05 M phosphate buffer (pH 7.0) and centrifugation was further conducted to prepare washed cells.

The whole amount of the washed cells described above was added to 5 ml of 0.3 M phosphate buffer (adjusted final pH to 7.0) containing 50 mM of orotidine or 5'-monoorotidic acid (hereafter simply referred to as orotidic acid) followed by reacting at 60° C. for 5 hours. The concentration of ribose-1-phosphoric acid produced in each reaction solution was measured by a known method using high performance liquid chromatography. The results are shown in Table 1.

TABLE 1

| Strain | | Ribose-1-phosphoric Acid Produced from Orotidine (mg/dl) | Ribose-1-phosphoric Acid Produced from Orotidic Acid (mg/dl) |
|---|---|---|---|
| Arthrobacter citreus | ATCC 11624 | 30 | 25 |
| Bacillus subtilis | IFO 3134 | 90 | 72 |
| Cellulomonas flavigena | ATCC 488 | 28 | 18 |
| Brevibacterium ammoniagenes | ATCC 6872 | 29 | 20 |
| Corynebacterium flavescens | ATCC 10340 | 31 | 21 |
| Escherichia coli | ATCC 12814 | 92 | 83 |
| Nocardia asteroides | ATCC 19247 | 27 | 25 |
| Planococcus eucinatus | FERM P-9133 | 26 | 20 |
| Pseudomonas rubescens | ATCC 12099 | 25 | 19 |
| Vibrio metschnikovii | ATCC 7708 | 75 | 60 |
| Xanthomonas campestris | ATCC 11765 | 29 | 27 |
| Serratia rubefaciens | FERM P-9134 | 76 | 70 |
| Streptomyces tanashiensis | ATCC 15238 | 32 | 30 |
| Erwinia carotovora | (FERM P-9135) (FERM BP-1548) | 305 | 250 |

Example 2

The whole amount of washed cells (corresponding to 5 ml of the culture solution) of microorganisms shown in Table 2 prepared by culturing them in a manner similar to Example 1 was added to 5 ml of 0.3 M phosphate buffer (adjusted final pH to 7.0) containing 50 mM of orotidine or orotidic acid and 50 mM of 1,2,4-triazole-3-carboxamide followed by reacting at 60° C. for 5 hours. The concentration of ribavirin produced in each reaction solution was measured by a known method using high performance liquid chromatography. The results are shown in Table 2.

TABLE 2

| Strain | | Ribavirin Produced from Orotidine (mg/dl) | Ribavirin Produced from Orotidic Acid (mg/dl) |
|---|---|---|---|
| Bacillus subtilis | IFO 3134 | 22 | 20 |
| Escherichia coli | ATCC 12814 | 44 | 38 |
| Planococcus eucinatus | FERM P-9133 | 31 | 27 |
| Pseudomonas rubescens | ATCC 12099 | 23 | 19 |
| Vibrio metschnikovii | ATCC 7708 | 35 | 28 |
| Serratia rubefaciens | FERM P-9134 | 67 | 60 |
| Erwinia carotovora | (FERM P-9135) (FERM BP-1538) | 258 | 232 |

Example 3

The whole amount of washed cells (corresponding to 5 ml of the culture solution) of

| Erwinia carotovora | FERM P-9135 |
| | FERM BP-1538 | prepared by culturing in a manner similar to Example 1 was added to 5 ml of 0.3 M phosphate buffer (adjusted final pH to 7.0) containing 30 mM of orotidine and 30 mM of 1,2,4-triazole-3-carboxamide followed by reacting at 60° C. for 20 hours. As a result, 0.52 g/dl (yield, 71%) of ribavirin was produced.

Example 4

The whole amount of washed cells (corresponding to 5 ml of the culture solution) of microorganisms shown in Table 4 prepared by culturing them in a manner similar to Example 1 was added to 5 ml of 0.3 M phosphate buffer (adjusted final pH to 7.0) containing 50 mM of orotidine or orotidic acid and 50 mM of 1,2,4-triazole-3-carboxamide. The whole amount of washed cells (corresponding to 5 ml of the culture solution) of Enterobacter cloacae ATCC 13047 (microorganism capable of producing ribavirin from ribose-1-phosphoric acid and 1,2,4-triazole-3-carboxamide, cf. Published Unexamined Japanese Patent Application No. 1746593/82) prepared by culturing it in a manner similar to Example 1 was added to each reaction solution followed by reacting at 60° C. for 5 hours. The concentration of ribavirin produced was measured in a manner similar to Example 2. The results are shown in Table 4.

TABLE 4

| Strain | | Ribavirin Produced from Orotidine (mg/dl) | Ribavirin Produced from Orotidic Acid (mg/dl) |
|---|---|---|---|
| Arthrobacter citreus | ATCC 11624 | 39 | 33 |
| Bacillus subtilis | IFO 3134 | 51 | 45 |
| Cellulomonas flavigena | ATCC 488 | 64 | 50 |
| Brevibacterium ammoniagenes | ATCC 6872 | 26 | 20 |
| Corynebacterium flavescens | ATCC 10340 | 27 | 22 |
| Escherichia coli | ATCC 12814 | 90 | 80 |
| Nocardia asteroides | ATCC 19247 | 40 | 34 |
| Planococcus eucinatus | FERM P-9133 | 22 | 15 |
| Pseudomonas rubescens | ATCC 12099 | 26 | 19 |

TABLE 4-continued

| Strain | | Ribavirin Produced from Orotidine (mg/dl) | Ribavirin Produced from Orotidic Acid (mg/dl) |
|---|---|---|---|
| Vibrio metschnikovii | ATCC 7708 | 38 | 29 |
| Xanthomonas campestris | ATCC 11765 | 24 | 22 |
| Serratia rubefaciens | FERM P-9134 | 85 | 77 |
| Streptomyces tanashiensis | ATCC 15238 | 25 | 21 |
| Erwinia carotovora | FERM P-9135 FERM BP-1538 | 268 | 243 |

The concentration of ribavirin produced in each reaction solution was measured by a known method using high performance liquid chromatography. The results are shown in Table 2.

Example 5

The whole amount of washed cells (corresponding to 5 ml of the culture solution) of

| Erwinia carotovora | FERM P-9135 FERM BP-1538 |
|---|---| prepared by culturing the same in a manner similar to Example 1 was added to 5 ml of 0.3 M phosphate buffer (adjusted final pH to 7.0) containing 50 mM of orotidine or orotidic acid and 50 mM of 1,2,4-triazole-3-carboxamide. The whole amount of washed cells (corresponding to 5 ml of the culture solution) of microorganisms shown in Table 5 prepared by culturing them in a manner similar to Example 1 was added to each reaction solution to prepare 28 kinds of reaction solutions shown in Table 5. Each reaction solution followed was reacted at 60° C. for 5 hours. The concentration of ribavirin produced was measured in a manner similar to Example 2. The results are shown in Table 5.

TABLE 5

| Strain | | Ribavirin Produced from Orotidine (mg/dl) | Ribavirin Produced from Orotidic Acid (mg/dl) |
|---|---|---|---|
| Pseudomonas diminuta | ATCC 11568 | 135 | 128 |
| Flavobacterium rhenanum | CCM 298 | 196 | 185 |
| Achromobacter lacticum | CCM 69 | 208 | 197 |
| Salmonella schottmuelleri | ATCC 8759 | 220 | 202 |
| Erwinia herbicola | ATCC 14536 | 260 | 240 |
| Proteus vulgaris | FERM P-4795 | 130 | 111 |
| Bacterium cadaveria | ATCC 9760 | 265 | 247 |
| Xanthomonas citri | FERM P-3396 | 180 | 173 |
| Citrobacter freundii | ATCC 8090 | 276 | 265 |
| Mycoplana dimorpha | ATCC 4279 | 45 | 38 |
| Escherichia coli | ATCC 10798 | 190 | 160 |
| Enterobacter cloacae | ATCC 13047 | 265 | 240 |
| Serratia marcescens | IFO 3046 | 185 | 155 |
| Klebsiella pneumoniae | ATCC 9621 | 275 | 260 |
| Micrococcus luteus | ATCC 398 | 160 | 148 |
| Corynebacterium michiganens | ATCC 7429 | 120 | 111 |
| Bacillus brevis | ATCC 8185 | 80 | 72 |
| Cellulomonas flavigena | ATCC 8183 | 245 | 222 |
| Arthrobacter globiformis | ATCC 8010 | 230 | 218 |
| Brevibacterium ammoniagenes | ATCC 6871 | 130 | 125 |
| Alcaligenes metalcaligenes | ATCC 13270 | 40 | 32 |
| Sporosarcina ureae | ATCC 6473 | 85 | 69 |
| Aeromonas salmonicida | ATCC 14174 | 192 | 181 |
| Candida tropicalis | ATCC 14056 | 145 | 128 |
| Saccharomyces cerevisiae | ATCC 2601 | 95 | 88 |
| Staphylococcus epidermidis | ATCC 155 | 220 | 205 |
| Kurthia zophii | ATCC 6900 | 40 | 33 |
| Vibrio metchnikovii | ATCC 7708 | 120 | 107 |

By the methods of the present invention, ribavirin and ribose-1-phosphoric acid which is a precursor of ribavirin can be efficiently produced in high yields. Therefore, ribavirin having an excellent antiviral effect can be supplied at low costs.

The invention now being fully described, it will be apparent to one of ordinary skill in the art that many changes and modifications can be made thereto without departing from the spirit or scope of the invention as set forth herein.

What is claimed as new and desired to be secured by Letters Patent of the United States is:

1. A method for producing ribavirin, which comprises contacting:
    (a) a microorganism, belonging to a genus selected from the group consisting of Bacillus, Escherichia, Planococcus, Pseudomonas, Vibrio, Serratia and Erwinia, with
    (b) orotidine, orotidic acid, or a slat thereof; an inorganic phosphoric acid or a salt thereof; and 1,2,4-triazole-3-carboxamide or a salt thereof, in an aqueous solvent to produce ribavirin,
wherein said microorganism is capable of producing ribavirin from orotidine, orotidic acid or a slat thereof; an inorganic phosphoric acid or a salt thereof; and 1,2,4-triazole-3-carboxamide or a salt thereof.

2. The method of claim 1, wherein said microorganism is Erwinia carotovora.

3. A method for producing ribavirin, which comprises contacting:
    (a) a first microorganism belong to a genus selected from the group consisting of Arthrobacter, Bacillus, Cellulomonas, Brevibacterium, Corynebacterium, Escherichia, Nocardia, Planococcus, Pseudomonas, Vibrio, Xanthomonas, Serratia, Streptomyces, and Erwinia, and
    (b) a second microorganism belonging to a genus selected from the group consisting of Pseudomonas, Flavobacterium, Achromobacter, Salmonella, Citrobacter, Escherichia, Sporosarcina, Alcaligenes, Enterobacter, Aeromonas, Arthrobacter, Brevibacterium, Serratia, Erwinia, Proteus, Corynebacterium, Cellulomonas, Xanthomonas, Klebsiella, Micrococcus, Bacillus, Bacterium, Candida, Saccharomyces, Staphylococcus, Kurthia, Vibrio, and Mycoplana, each with
    (c) orotidine, orotidic acid or a salt thereof; an inorganic phosphoric acid or a salt thereof; and 1,2,4-triazole-3-carboxamide or a salt thereof, in an aqueous solvent to produce ribavirin,
wherein said first microorganism is capable of producing ribose-1-phosphoric acid from orotidine, orotidic acid or a salt thereof and an inorganic phosphoric acid or a salt thereof, and said second microorganism is capable of producing ribavirin from ribose-1-phosphoric acid or a salt thereof, an inorganic phosphoric acid or a salt thereof, and 1,2,4-triazole-3-carboxamide or a salt thereof.

4. The method of claim 3, wherein said first microorganism is Erwinia carotovora and said second microorganism is Klebsiella pneumoniae.

* * * * *

UNITED STATES PATENT AND TRADEMARK OFFICE
CERTIFICATE OF CORRECTION

PATENT NO. : 4,968,606
DATED : NOVEMBER 6, 1990
INVENTOR(S) : YOKOZEKI ET AL

It is certified that error appears in the above-identified patent and that said Letters Patent is hereby corrected as shown below:

Column 4, line 6, "1,2,4-triazole-3 carboxamide" should read --1,2,4-triazole-3-carboxamide--.

Column 4, line 54, "1,2,4-triazole-3car-" should read --1,2,4-triazole-3-car---.

Column 8:
Claim 1, line 29, "slat" should read --salt--;

line 12, "slat" should read --salt--.

Signed and Sealed this

First Day of September, 1992

Attest:

DOUGLAS B. COMER

Attesting Officer

Acting Commissioner of Patents and Trademarks